(12) United States Patent
Murdoch

(10) Patent No.: US 7,208,004 B2
(45) Date of Patent: Apr. 24, 2007

(54) APPARATUS AND METHOD FOR GRIPPING AND MANIPULATING A SURGICAL NEEDLE

(76) Inventor: Mervyn John Murdoch, 96 Rialannah Road, Mt Nelson (AU) 7007

( * ) Notice: Subject to any disclaimer, the term of this patent is extended or adjusted under 35 U.S.C. 154(b) by 0 days.

(21) Appl. No.: 10/160,520

(22) Filed: Jun. 12, 2002

(65) Prior Publication Data

US 2003/0045833 A1     Mar. 6, 2003

(51) Int. Cl.
*A61B 17/32* (2006.01)
(52) U.S. Cl. ............................................... 606/205
(58) Field of Classification Search .................. None
See application file for complete search history.

(56) References Cited

U.S. PATENT DOCUMENTS

| | | | | |
|---|---|---|---|---|
| 2,504,202 A | * | 4/1950 | Kadavy | 606/147 |
| 3,971,386 A | * | 7/1976 | Yamada | 606/133 |
| 4,635,638 A | * | 1/1987 | Weintraub et al. | 606/147 |
| 5,342,375 A | * | 8/1994 | Lemole | 606/148 |
| 5,620,460 A | * | 4/1997 | Smith | 606/205 |
| 5,645,552 A | * | 7/1997 | Sherts | 606/145 |
| 5,713,710 A | * | 2/1998 | Strong et al. | 414/139.5 |
| 5,746,757 A | * | 5/1998 | McGuire | 606/148 |
| 5,843,121 A | * | 12/1998 | Yoon | 606/206 |
| 5,891,161 A | * | 4/1999 | Graser | 606/148 |
| 2002/0013603 A1 | * | 1/2002 | Green | 606/205 |

* cited by examiner

*Primary Examiner*—Anhtuan T. Nguyen
*Assistant Examiner*—Bradford C Pantuck

(57) ABSTRACT

The invention consists of a hand gripping portion 11, a tissue manipulating portion 13 and a needle retaining means 16. The needle retaining means is placed proximal or adjacent to the tissue manipulating portion. It comprises a needle impervious sleeve 15, which contains a needle pervious material 18.

5 Claims, 14 Drawing Sheets

APPARATUS AND METHOD FOR GRIPPING AND MANIPULATING A SURGICAL NEEDLE

The present invention pertains to hand held medical instruments and method of use thereof, which are designed to position tissue in a suturing procedure. More particularly, the invention pertains to hand held medical instruments and method of use thereof, which are designed to receive and retain the movement of the pointed end portion of a surgical needle, as the surgical needle passes through a patient's tissue, and is herein described in that context. It is to be appreciated however, that the invention is not limited thereto.

The sewing of tissue is an important aspects of surgery.

There are basic stitch movements involved in most surgical sewing procedures. These basic stitch movements are as follows: gripping the shank portion of a needle with a needle holder, manipulating the needle holder to push the pointed end portion of the needle at least partly through the tissue, gripping the pointed end portion of the needle with a suitable gripping means, disengaging the shank portion of the needle from the needle holder, pulling the needle and the suture completely through the tissue, supporting the needle with a suitable means (e.g. fingers, forceps, etc.) re-gripping the shank portion of the needle with the needle holder and repeating the procedure as necessary.

Although these steps have been used for many years, there are problems associated therewith. For example, due to the inherent sharpness of the pointed end portion of the needle, extreme care has to be used when gripping the needle as it is passing through the tissue. Specifically, if the gripping means is the thumb and forefinger of a medical practitioner, the needle may puncture these appendages. This is of major concern to both the practitioner and the patient, especially with the growing awareness of the means by which viruses such as the AIDS virus and hepatitis can be transmitted. Notwithstanding the potential problems associated with the implementation of this gripping procedure, it is still used by many medical practitioners.

In an attempt to remedy this problem, many medical practitioners use a forceps-type apparatus to grip the pointed end portion of the needle. Although this approach keeps the practitioner's fingers from coming in direct contact with the needle's point, there are still problems associated therewith. For example, with this method it is difficult to manipulate and to orientate the needle so that it can be easily grasped in the needle holder. Also, the needle can easily slip from the grasp of the forceps, as there is metal to metal contact only. This complicates the suturing process.

Over the years, there have been other attempts to improve the manner by which a needle's point is gripped in the suturing procedure.

In one form (U.S. Pat. No. 3,878,848), a surgical needle capturing device, comprising a handle member and a body member which has sufficient resistance to be penetrated by a surgical needle, is described. Although this device will grasp the needle, there is nothing to prevent the needle from passing right through the body member, to expose the pointed end of the needle. Moreover, the device cannot be used to manipulate or hold tissue.

Another existing apparatus (U.S. Pat. No. 5,342,375) is designed to capture and manipulate the movement of surgical needles as they pass through tissue. The apparatus has a removable gripping body component, which is designed to rest against the tissue wall of a patient. This gripping body component has sufficient resistance to be penetrated by and grip, the needle's point.

Such an arrangement allows for a gripping member to be attached to a surgical instrument such as forceps, so that the instrument may be used in one of two ways. Firstly, the instrument performs the function it was initially designed for and secondly, the instrument may be used to retain and manipulate a needle after the suture has been passed. Whilst it is convenient that the one tool can perform two functions, the instrument is used as two separate instruments, which has been found to be relatively inconvenient in the context of conducting surgery. A surgeon needs to re-orient and re-grip the instrument before using the instrument to perform an alternate function (i.e. when switching between an instrument to position tissue and an instrument to receive and retain a surgical needle).

Another apparatus (U.S. Pat. No. 5,490,858) describes another needle capturing device. This device however cannot be used to hold or manipulate tissue, making it necessary for the practitioner to exchange this device with the forceps each time a suture is placed.

The discussion of the background to the invention herein is included to explain the context of the invention. This is not to be taken as an admission that any of the material referred to was published, known, or part of the common general knowledge as at the priority date of any of the claims.

It would be desirable to provide an apparatus which is capable of positioning tissue and is also capable of capturing, manipulating and orienting the movement of a surgical needle passing through the tissue of a patient.

It would also be desirable to provide an improved suturing method and a method of guarding the sharp end of the suture needle from injury to the practitioner or patient, when the needle is not being directed through tissue as part of the suturing process.

According to the present invention, there is provided a surgical instrument for gripping and manipulating a surgical needle, including a hand gripping portion, a tissue manipulating portion and a needle retaining means. The needle retaining means is placed proximal or adjacent to the tissue manipulating portion.

Preferably, the tissue manipulating portion includes a pair of connected arms. Preferably, at least one of the arms is permitted to move from an open position away from the other arm to a closed position next to or closely adjacent the other arm to enable the grasping of tissue therebetween.

Preferably the hand gripping portion includes means for reversibly moving the arms from an open position to a closed position.

In a particularly preferred form, each of the two arms includes a grasping section, proximal to the end of the arm.

The applicant envisages that in one particularly preferred form, the surgical instrument will be in the general configuration of forceps.

Most preferably, the needle retaining means is provided at, or closely adjacent the grasping section of the tissue manipulating portion.

In a particularly preferred form, the needle retaining means is releasably connected to one of the arms of the surgical instrument.

Alternatively, it is to be appreciated that the needle retaining means could be permanently attached to the surgical instrument, such as by welding or brazing. In still a further alternative, the needle retaining means could be integral with, or otherwise form, a structural arm of the forceps.

In a preferred form, the needle retaining means includes a needle pervious material. In one particular form, the needle retaining means is in the form of a rubber or rubber-like or silicone or silicone-like material. Alternatively a magnetic or spring loaded friction clamp could be used.

It is to be appreciated that the needle pervious material should be of sufficient resistance to be penetrated by and grip, the pointed end portion of a surgical needle, as the needle is passed through tissue.

Preferably, the needle retaining means includes a needle impervious casing, surrounding at least a portion of the needle pervious material. The applicant presently envisages that the needle impervious casing would be made of plastic or metal. Most preferably, the casing would include a needle receiving opening to enable the needle to be received by the needle pervious material.

In this one form, the casing could include a releasable connecting means for connecting the casing to the surgical instrument.

In one particularly desirable form, the casing of the needle retaining means is a flexible and resilient plastic sleeve having two longitudinal channels. One of the channels houses the needle pervious material. The other channel is provided as the means for releasably connecting the casing to one of the arms of the surgical instrument.

The present invention also relates to a method of conducting surgery using the aforementioned surgical instrument. Such a method includes the steps of positioning tissue to be sutured within the tissue manipulating portion, passing the point of a needle through the tissue and aligning the surgical instrument so that the needle retaining means is aligned with the point of the needle. Following this, the point of the needle is then passed into the needle retaining means and the surgical instrument is manipulated to pull the needle and attached suture through the tissue.

It is also to be appreciated that the present invention could be adapted for endoscopic use with a retaining means either attached to, or part of the tip of the shaft of the surgical instrument. In such an arrangement, it is envisaged that the surgical instrument would be in the form of forceps.

The present invention also relates to a unit for disposal of a needle retaining means, the unit including a casing and a retaining device for retaining at least one needle retaining means.

DETAILED DESCRIPTION OF THE DRAWINGS

Figure 1:
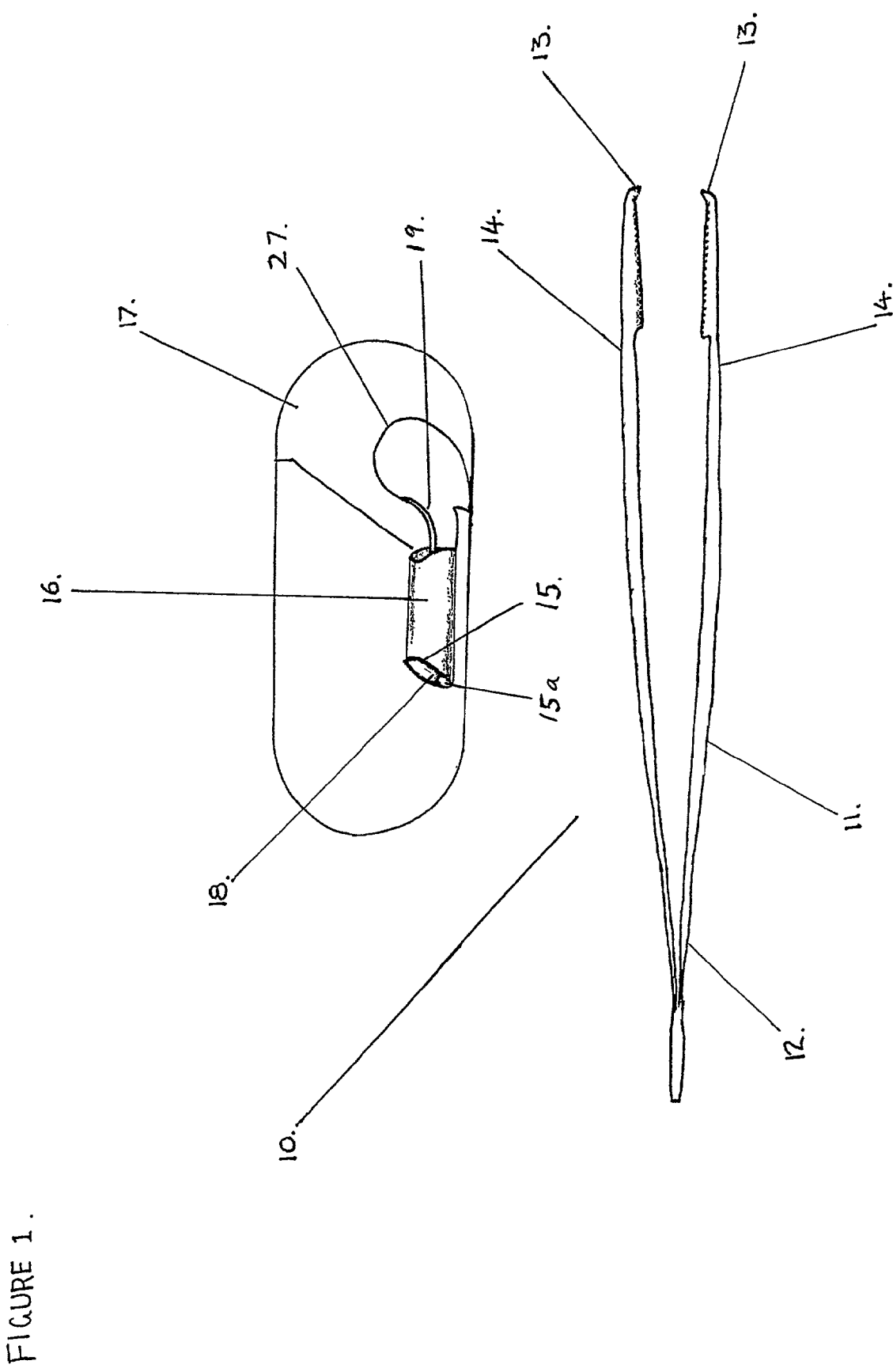
FIG. 1 illustrates a surgical instrument and a needle retaining means in a separated arrangement and with the needle retaining means placed on top of a possible packaging for the needle retaining means, needle and suture.

In FIG. 1 a surgical instrument 10 including forceps 11 is illustrated. The forceps 11 include a hand gripping portion 12 and a tissue manipulating portion 13. The tissue manipulating portion 13 includes a pair of arms 14. A disposable needle retaining means 16 is illustrated resting on a possible needle retaining means packaging 17, with needle 19 and suture 27. In the illustrated configuration the needle retaining means 16 is releasably connectable to the packaging 17.

The needle retaining means 16 includes a needle impervious casing 15 made of plastic or metal and a needle pervious rubber-like or silicone-like material 18 or alternatively a magnetic or spring loaded friction clamp, which is preferably sterilisable.

It is envisaged that for sterilising purposes, the needle retaining means 16 would be sterilised prior to use. Accordingly, it is envisaged that the needle retaining means 16 would be removed from its packaging 17 shortly before use.

The needle retaining means 16 includes a sleeve through which one of the forceps arms is inserted to connect the retaining means 16 and the forceps 11 together. A locking arrangement is included to retain the retaining means 16 and the forceps 11 connected together. This is in the form of a notch and groove arrangement or other arrangement. The needle retaining means 16 is disposable.

It is to be appreciated, however, that while the illustrated embodiment includes a disposable needle retaining means 16, the needle retaining means 16 need not be disposable. It could be reusable.

Figure 2:
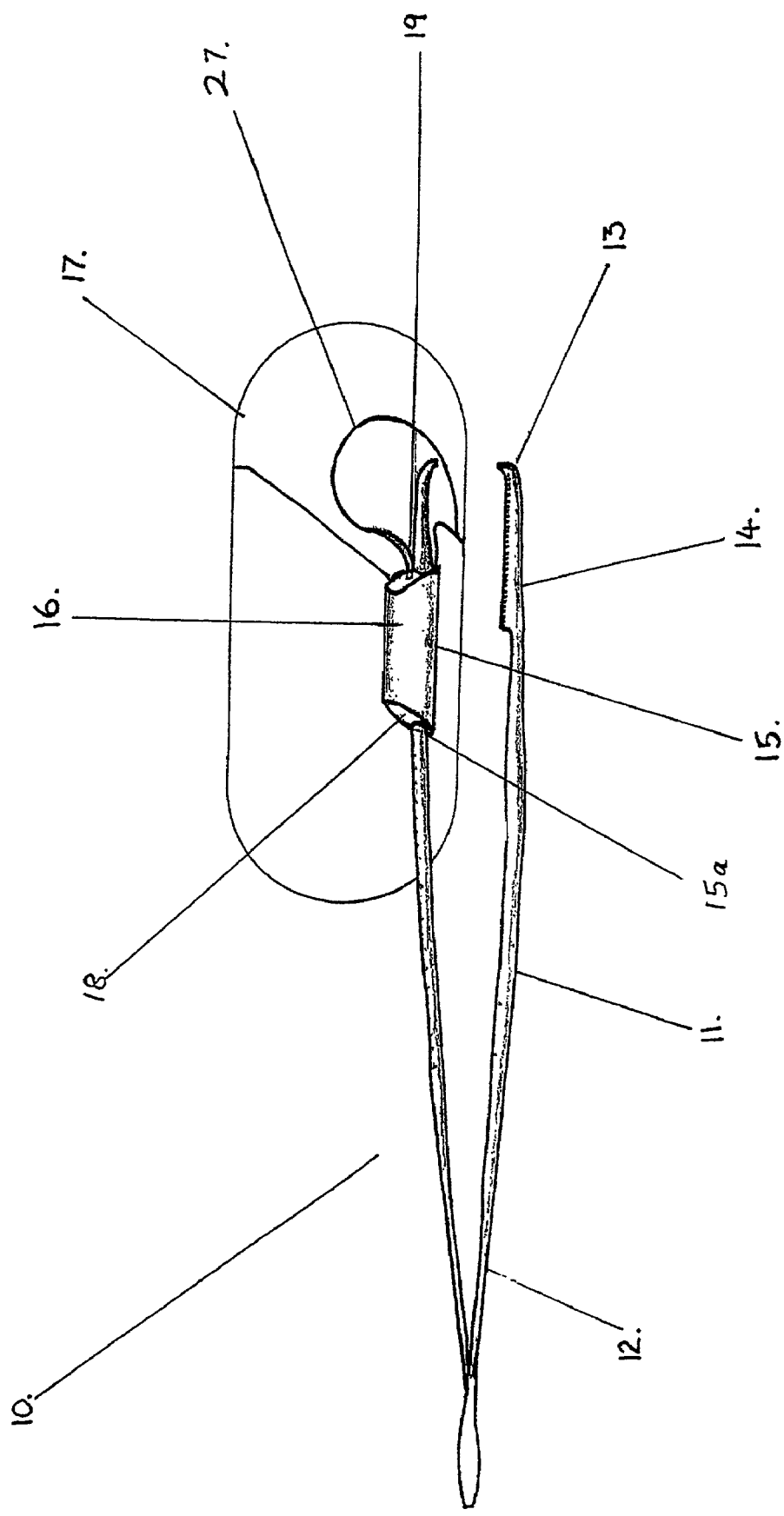
FIG. 2 is similar to FIG. 1, but with the surgical instrument now attached to the needle retaining means.

As illustrated in FIG. 2, immediately prior to surgery, the packaging 17 is opened and the retaining means 16 with needle 19 and suture 27 is removed by releasably connecting the forceps 11 to the needle retaining means 16, by inserting one arm of the forceps into a sleeve portion 15a of the needle retaining means 16.

Figure 3:
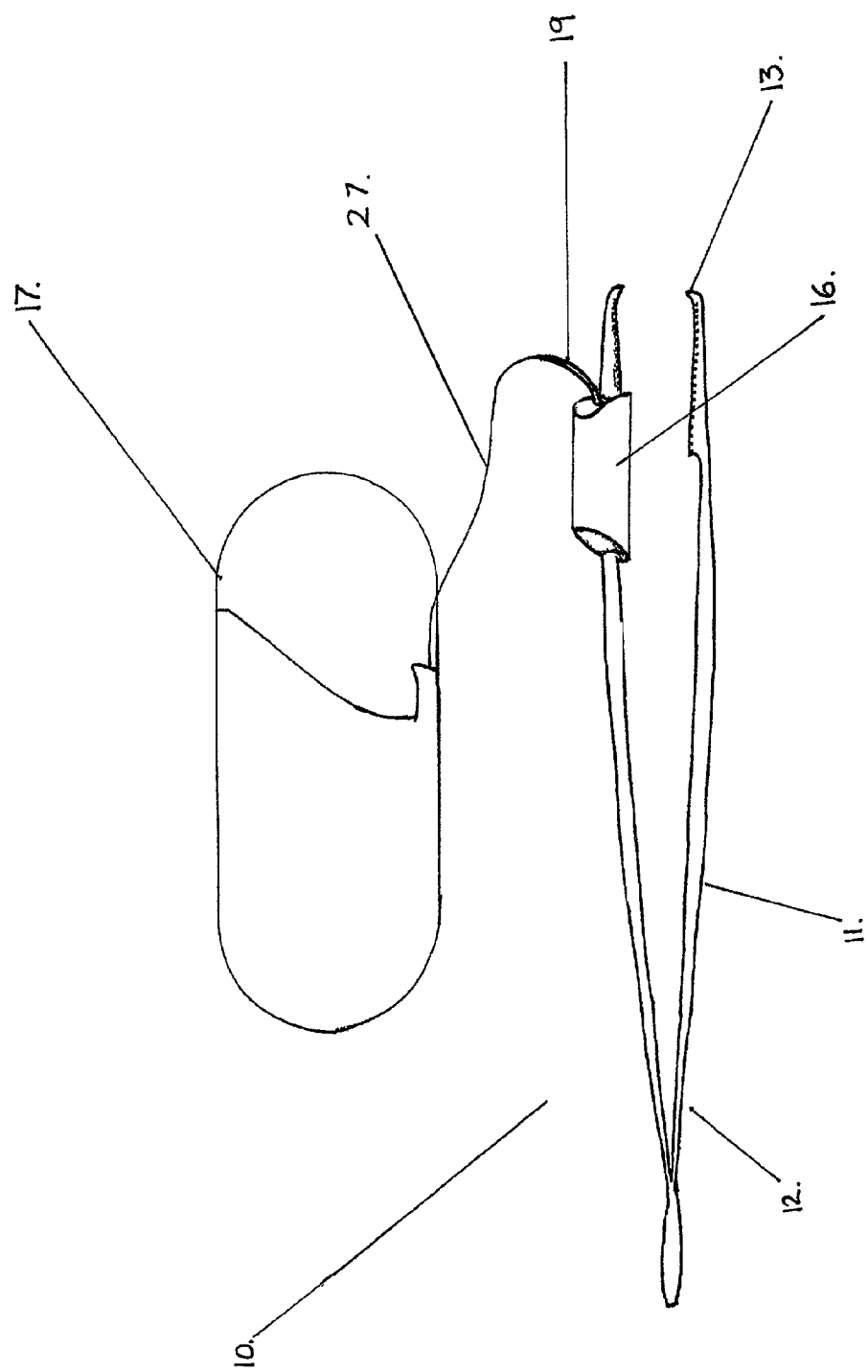
FIG. 3 illustrates the surgical instrument attached to the needle retaining means as in FIG. 2, but with the needle retaining means removed from its packaging.

FIG. 3 illustrates the needle retaining means 16 attached to the forceps 11 and removed from the needle retaining means packaging 17. As is illustrated in FIG. 2, it is envisaged that the needle retaining means 16 would be packaged with a needle 19 and a suture 27, attached to the needle 19. This is beneficial, because the needle 19 can be provided in an already orientated arrangement with respect to the forceps 11 and the needle retaining means 16, to enable for a simplified commencement by the surgeon or medical practitioner of the suturing process.

Figure 4:
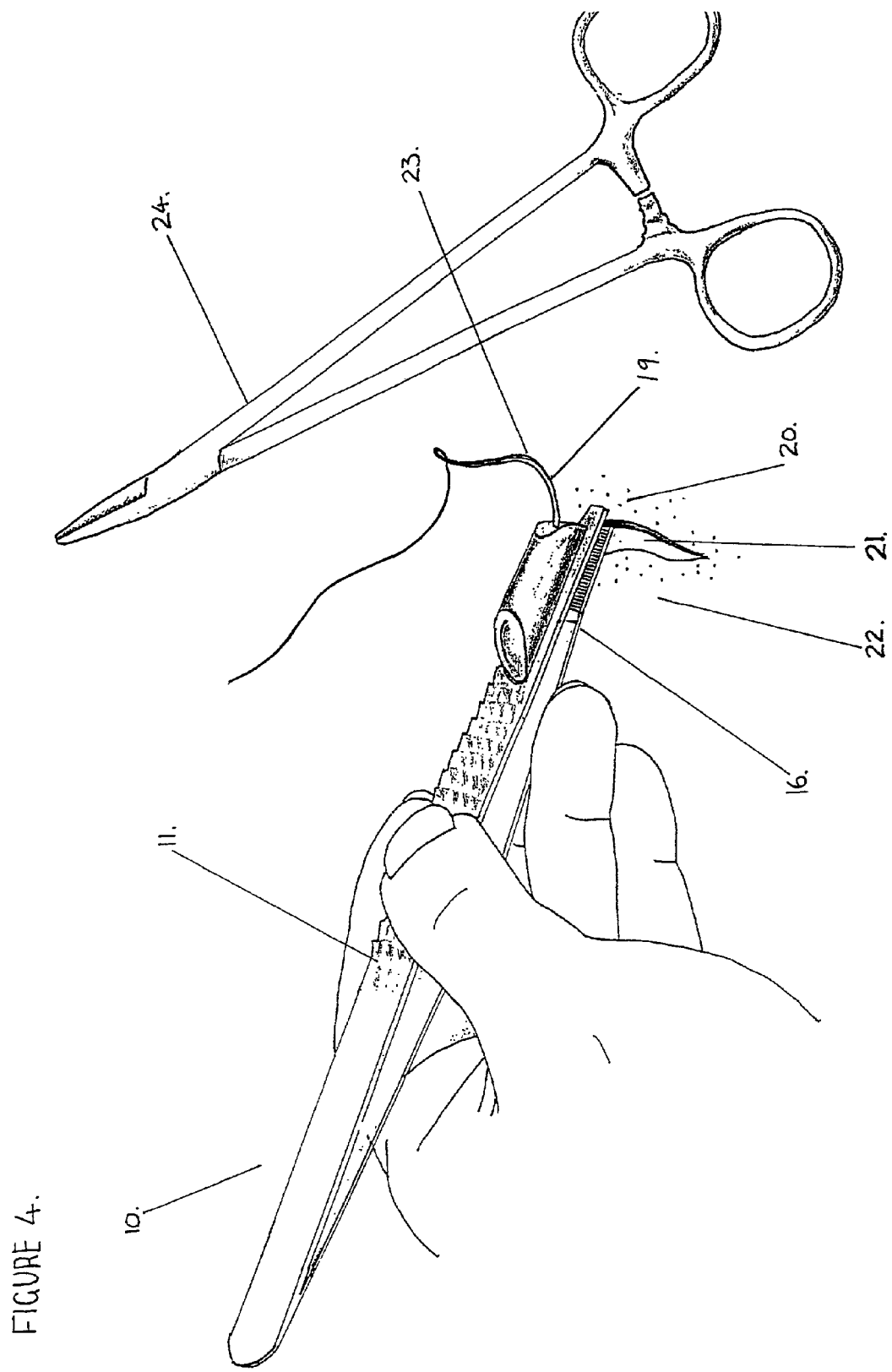
FIG. 4 illustrates the arrangement of FIG. 3 when used in a suturing procedure.

FIG. 4 illustrates the surgical instrument 10 in use and in a first position wherein a suture is about to be applied. In the example, the forceps 11 are clamping one side 20 of an opening in tissue 22. With the forceps 11, holding the side 20 of the opening 21 as illustrated, the needle 19, extends from the needle retaining means 16, in a conveniently aligned arrangement to enable the exposed end 23 of the needle 19, to be clamped by a needle holder 24, referred to as clamp to avoid confusion with the invention. In FIGS. 4 to 13, the needle retaining means 16 is shown as a metal casing, which is an integral part of the device, with the needle pervious material as silicone.

Figure 5:
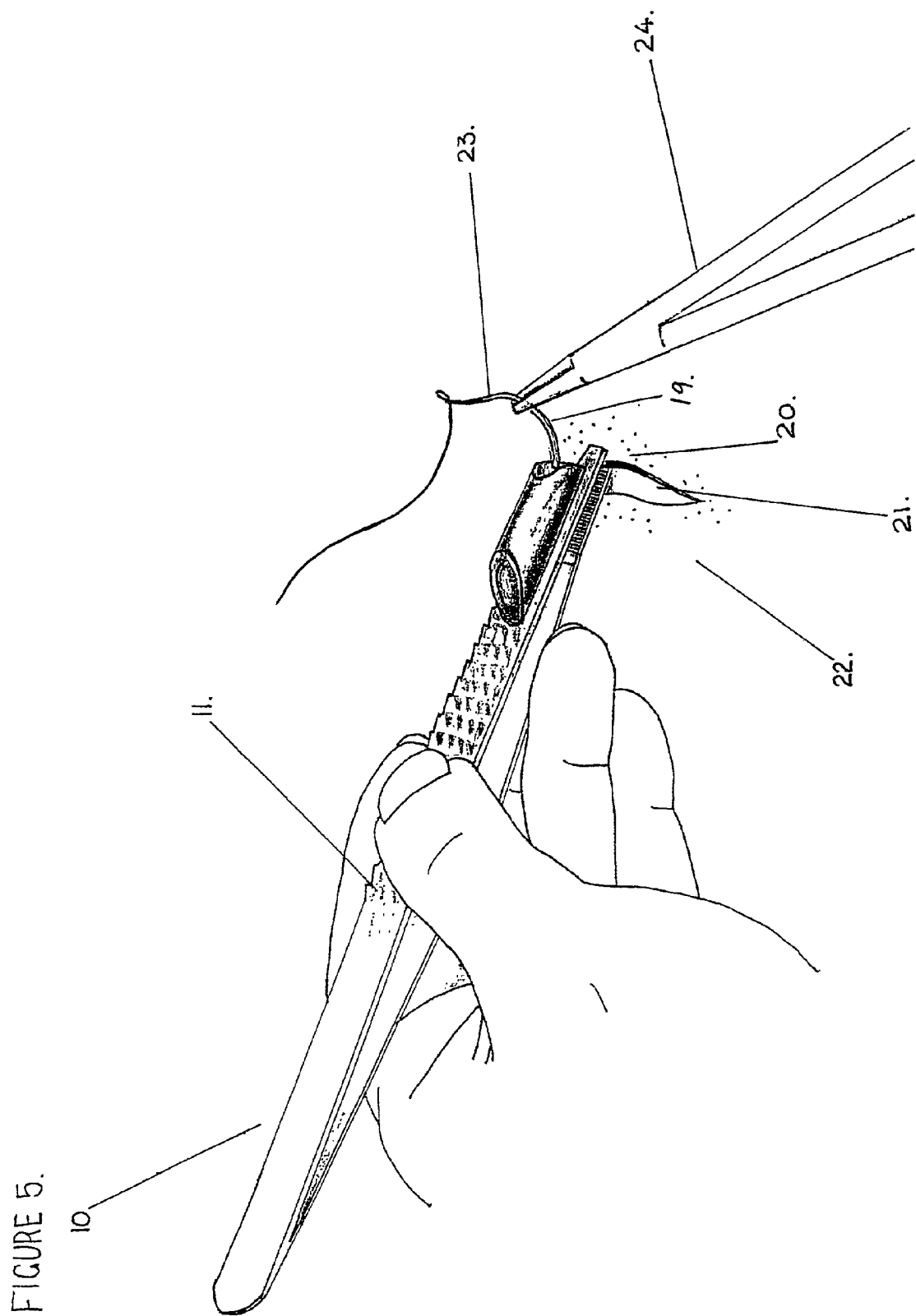
FIG. 5 illustrates another step in the suturing procedure.

FIG. 5 illustrates the next step in the suturing process, whereby the clamp 24 is clamped onto the exposed end 23 of the needle 19.

Figure 6:
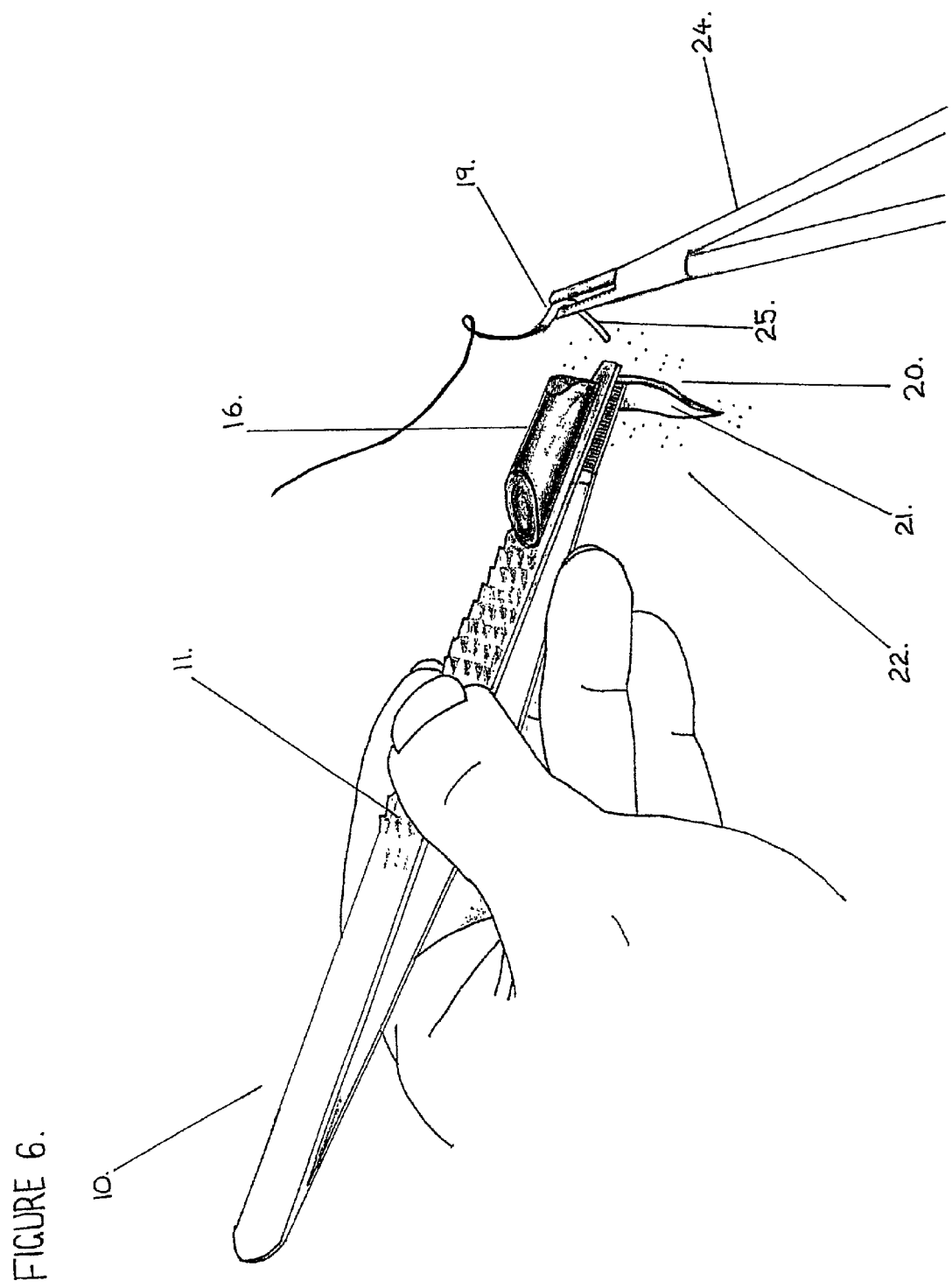
FIG. 6 illustrates a further step in the suturing procedure.

FIG. 6 illustrates the next step in the suturing process, whereby the clamp 24 is used to remove the needle 19 from the needle retaining means 16. The clamp 24 is then used to insert the sharp end 25 of the needle 19 through the tissue 22 on the side 20 of the tissue opening 21.

Figure 7:
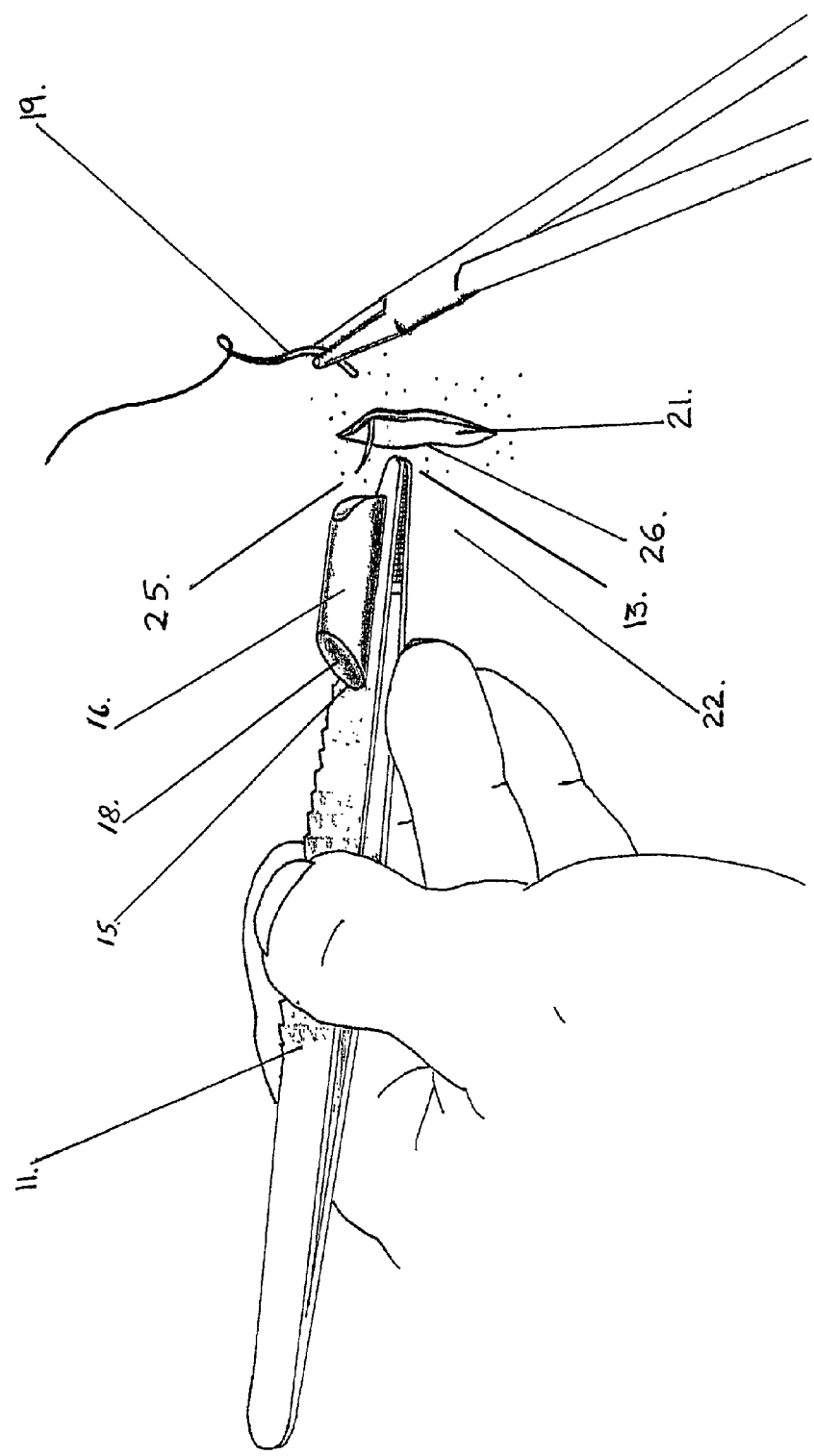
FIG. 7, likewise, illustrates a further step in the suturing procedure.

FIG. 7 then illustrates the needle 19 being further inserted through the tissue 22, to the point where the sharp end 25 of the needle 19 extends through the opening 21 being sutured and with the forceps 11 now gripping the other side 26 of the opening 21.

Figure 8:
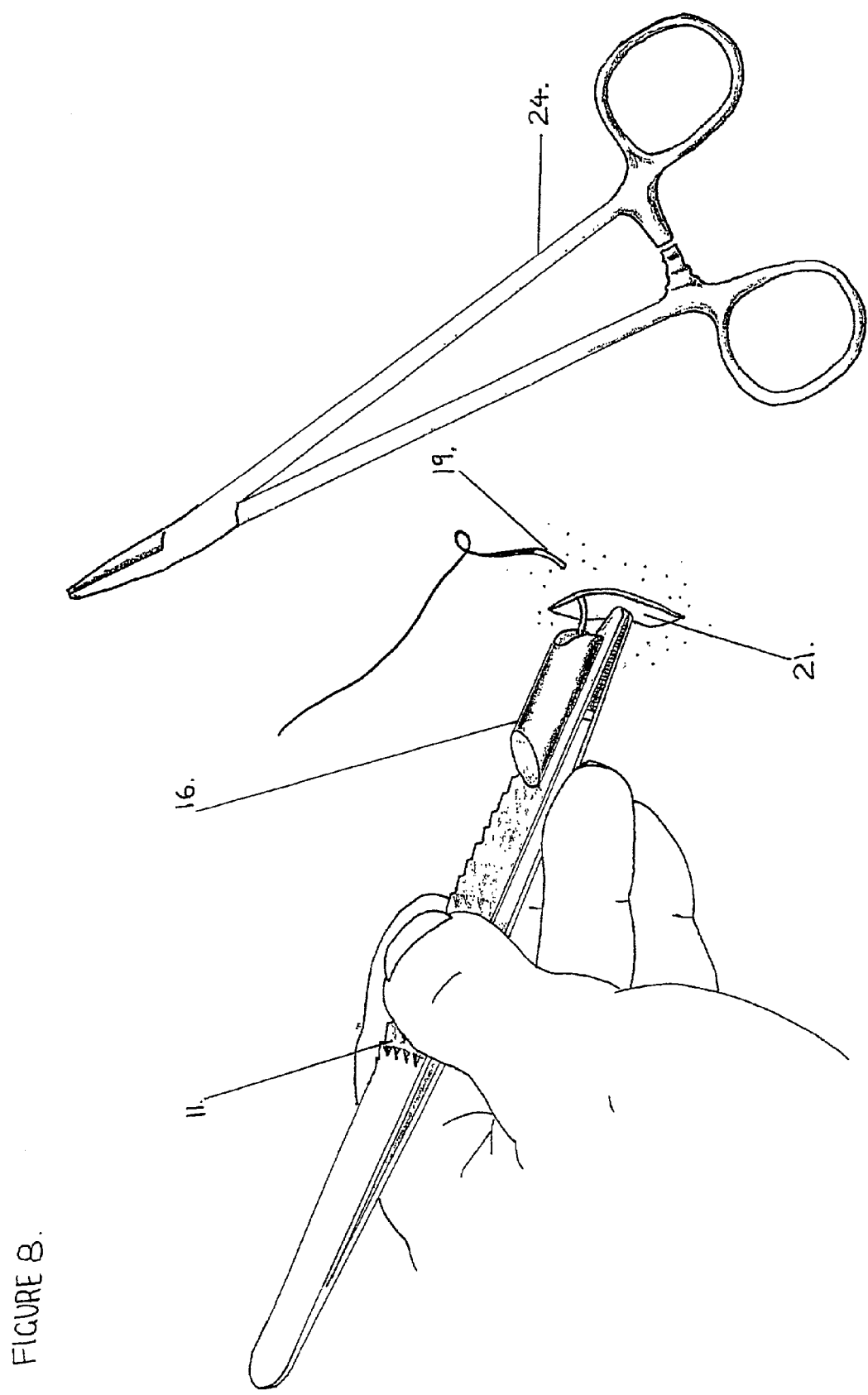
FIGS. 8, 9, 10, 11, 12, 13 each likewise illustrate further steps in the suturing procedure.

FIG. 8 illustrates the needle 19 having been inserted, using the clamp 24 to again be retained by the needle retaining means 16.

Figure 9:
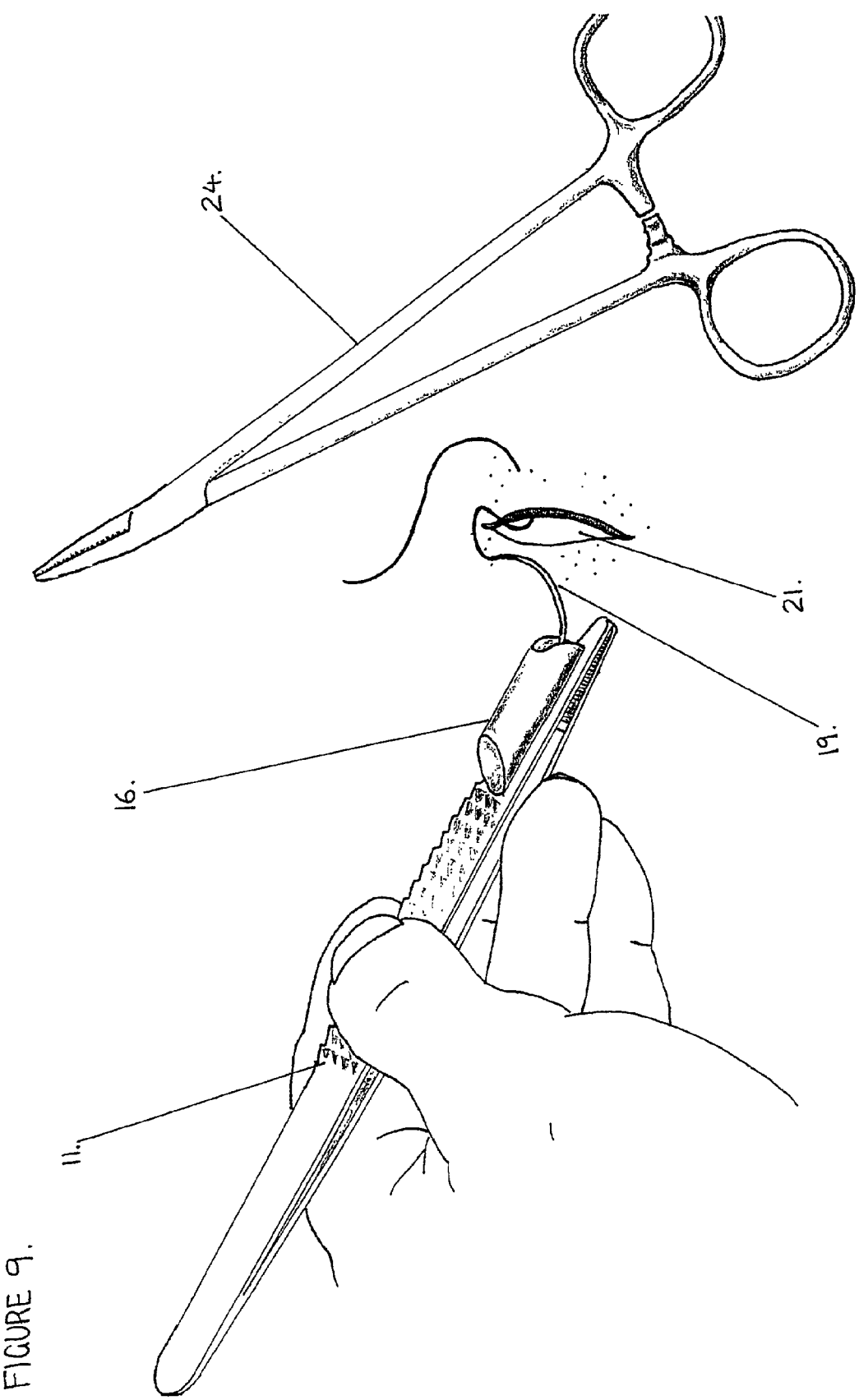

In this position, the needle retaining means 16 can then be used to pull the needle 19 all the way through the opening 21 being sutured, as illustrated in FIG. 9.

Figure 10:
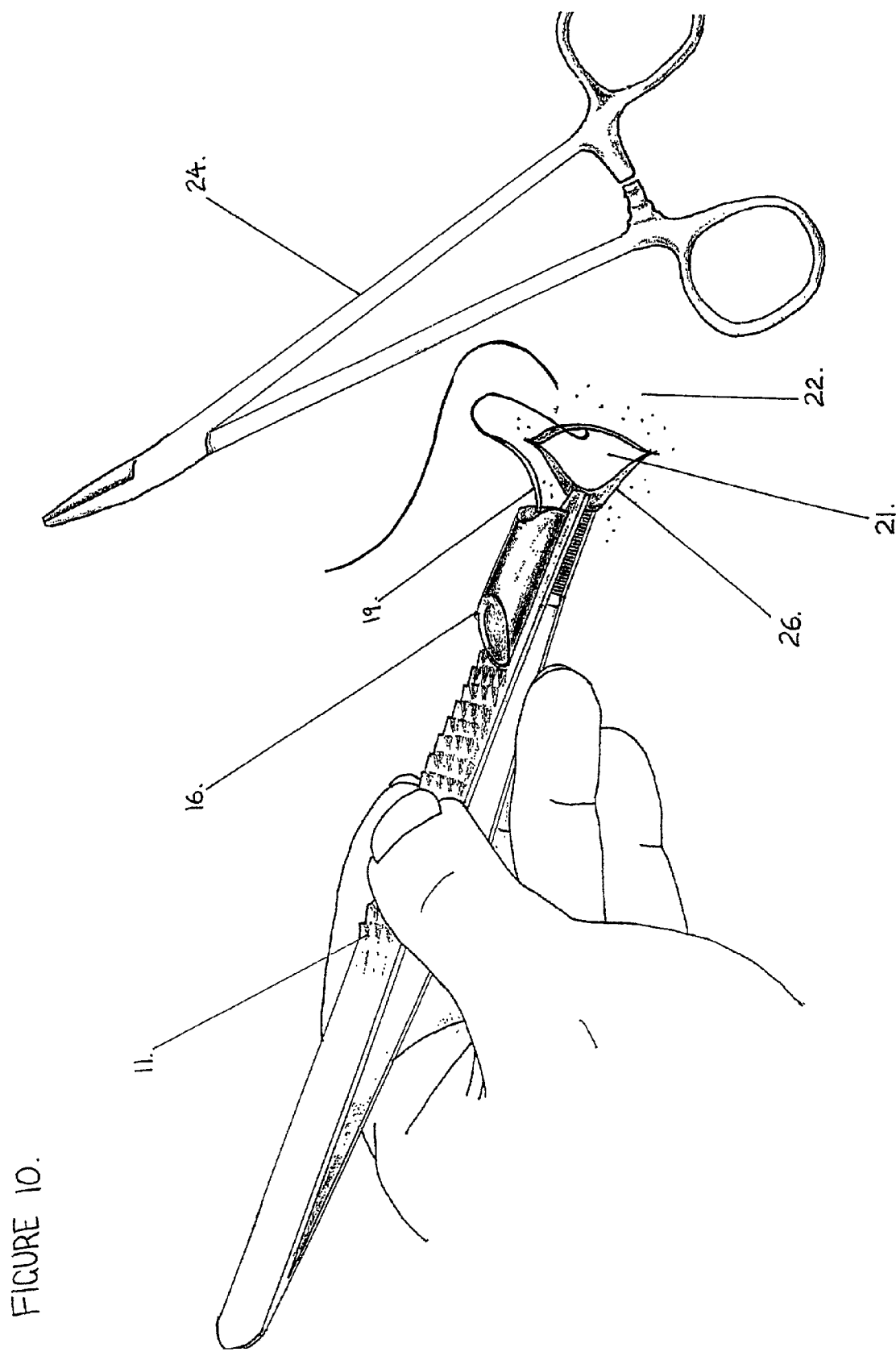
Figure 11:
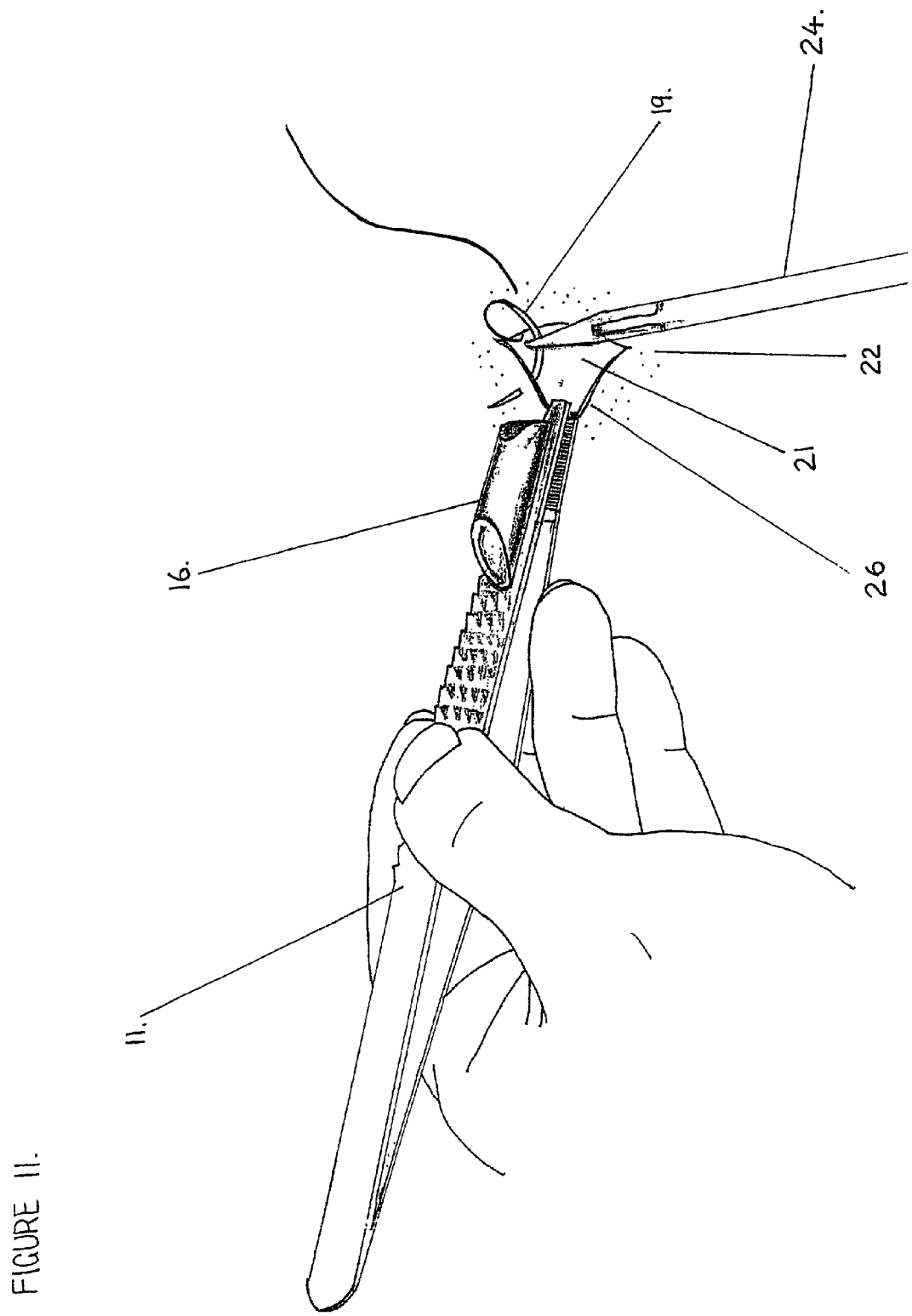

Once the needle 19 is pulled all the way through the opening 21, the forceps 11 are then used to grasp the other side 26 of the opening 21 being sutured. This is illustrated in FIG. 10. In so doing, the needle 19 is conveniently aligned with respect to the forceps 11, such that it can be easily clamped by the clamp 24, removed and then inserted through the tissue 22 on the other side 26 of the opening 21, as illustrated in FIG. 11. Again the needle 19 is inserted through the tissue 22 and into the needle retaining means 16.

Figure 12:
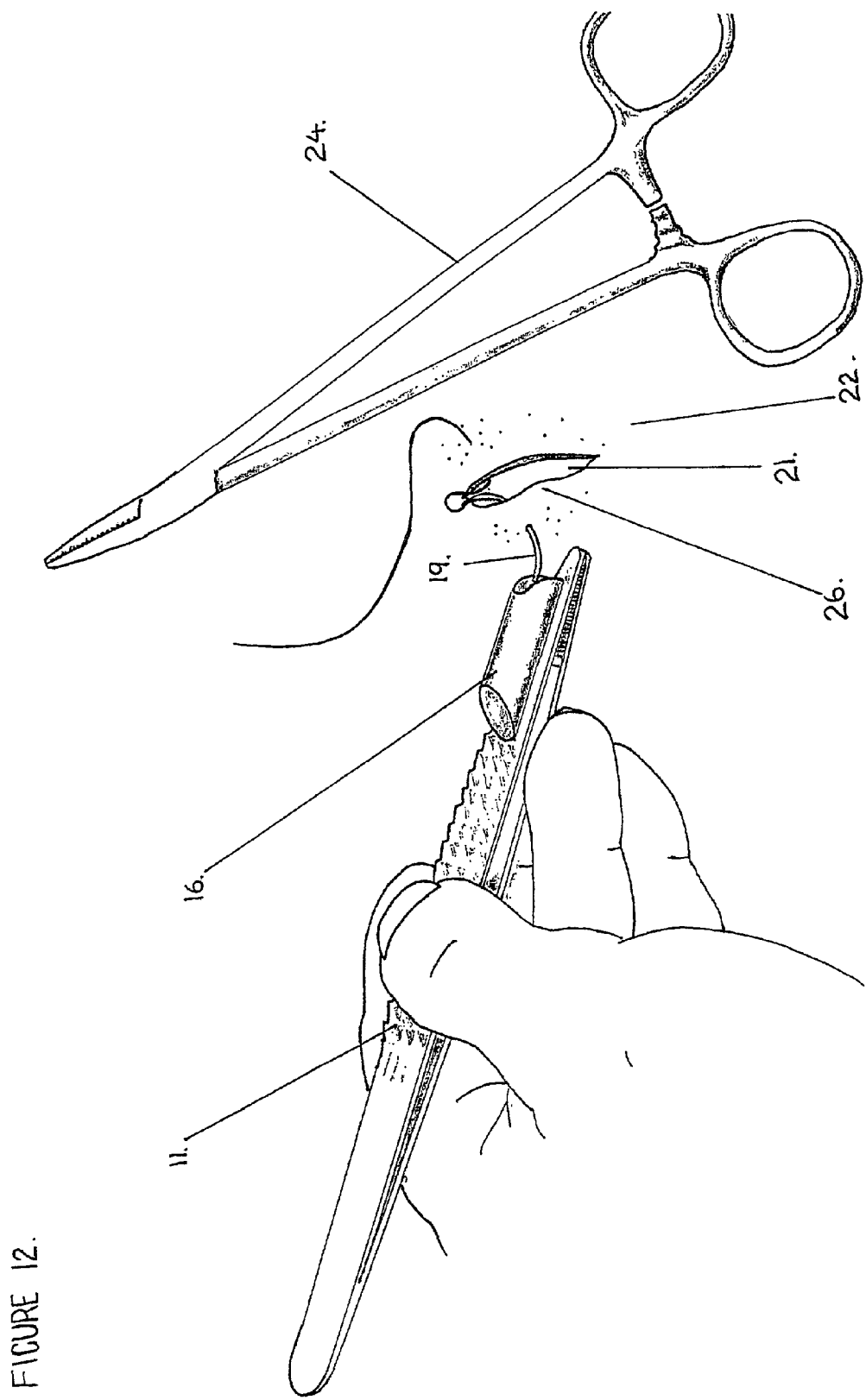

From this position, the needle 19 can then be pulled through the tissue 22 on the other side 26 of the opening 21 by the needle retaining means 16, as illustrated in FIG. 12.

Figure 13:
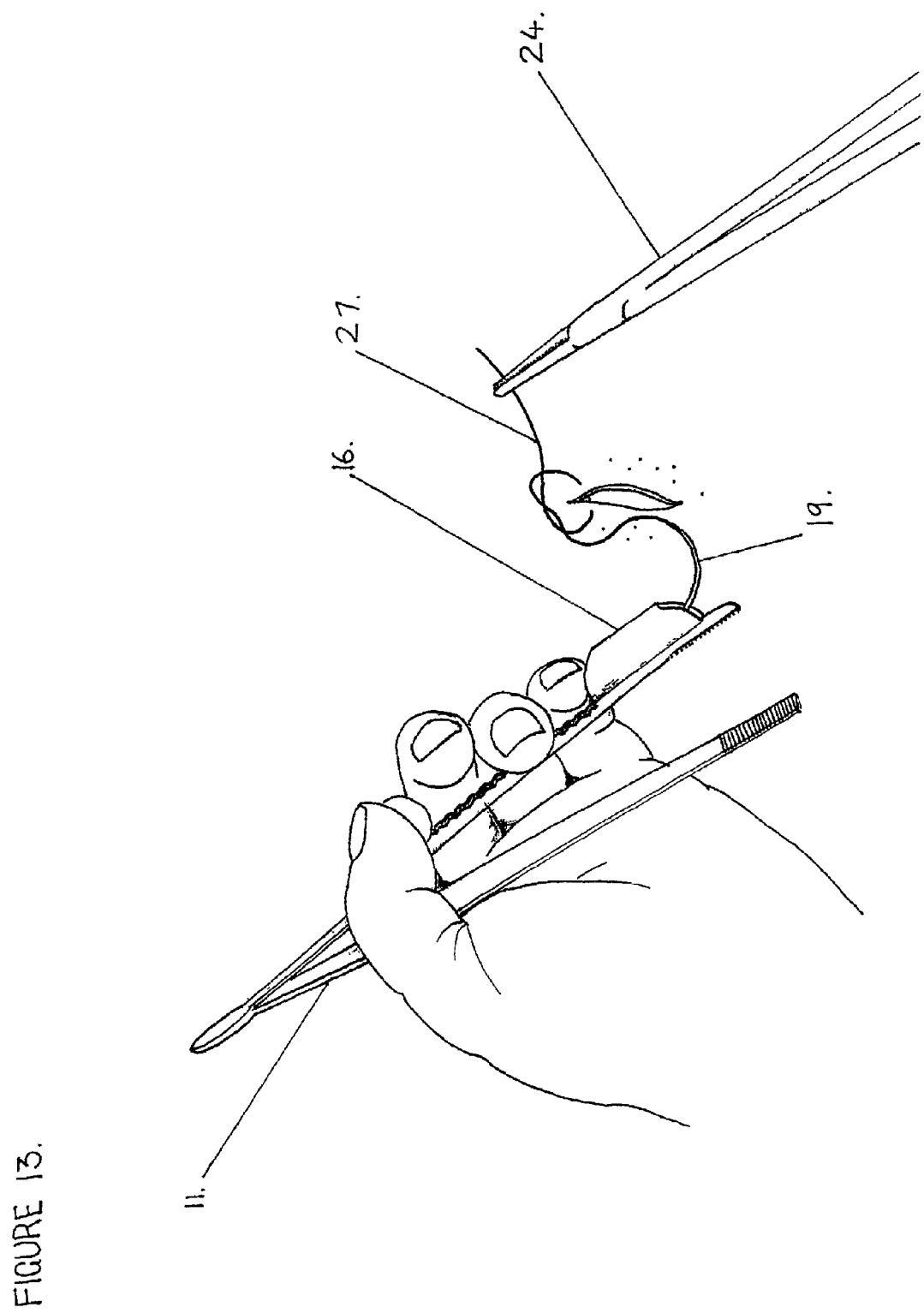

FIG. 13 illustrates how the present invention conveniently and safely enables the suture 27 to be tied at the end of the suturing process. The operator is able to comfortably hold the forceps 11 in one hand and the clamp 24 in the other hand, to enable the suture 27 to be tied without having to be concerned with needle stick injuries that could occur, if the end of the needle was exposed.

Thus, it can be seen that the point of the needle 19 remains guarded at all times, except for when it passed through the tissue and into the needle retaining means 16.

The illustrated embodiment permits a surgeon to alternate between positioning tissue and manipulating a surgical needle, without having to re-grip the instrument and the instrument requires only a small amount of movement. In fact, the instrument of the present invention permits for the simultaneous positioning of tissue for suturing and the retention of the point of the needle, after it is passed through the patient's tissue. For example, when using forceps suturing in a deep wound, the surgeon can pass the needle through the tissue at one side of the wound and into the needle retaining means, whilst using the forceps to retract the other side of the wound. This has the advantage of protecting tissue and reducing the likelihood of needle stick injuries.

The present invention also has the advantage that when the instrument is used to position tissue near the suture location, the needle is presented near the suturing location in the appropriate orientation.

In microsurgery, where suturing is done using a microscope to magnify the image, it is very easy to misplace the suture needle out of the microscope's field. This is very inconvenient, because the surgeon has to move away from the microscope to accommodate normal vision to find the needle. This is not only time consuming, but tiring for the surgeon. With this invention, the needle can be held in the retaining device until needed for the next suture and is therefore easily located or returned to the field of surgery, without the need for the surgeon to re-accommodate his vision on each occasion.

Even when a suture is tied, the needle is held in the retaining member and remains guarded. The surgical instrument can then be passed from the surgeon to other staff members and the needle remains guarded.

Figure 14:
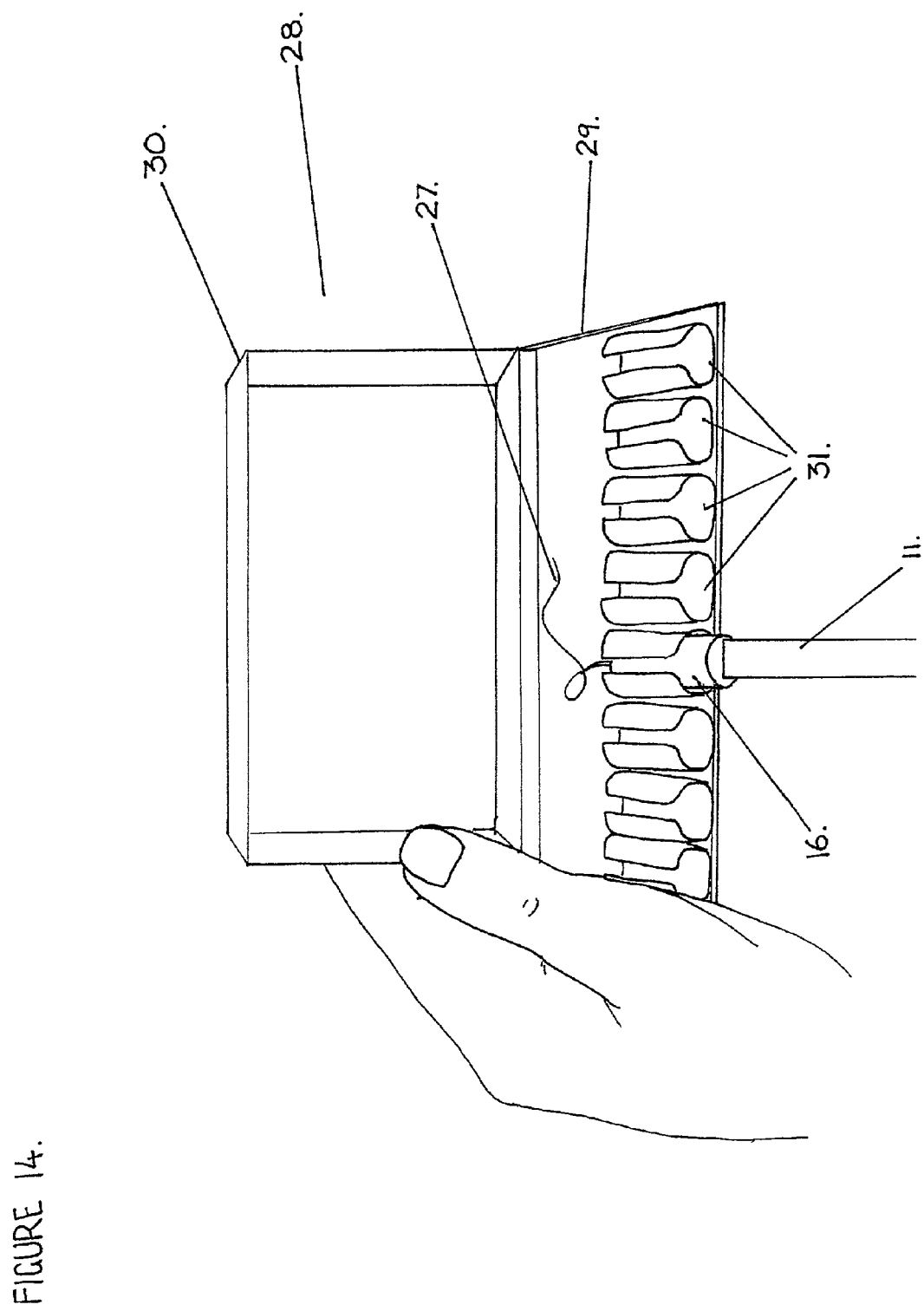
FIG. 14 illustrates a disposal unit for disposal of the needle retaining means, with a needle retaining means being inserted into the unit.

FIG. 14 illustrates one embodiment of a disposal device 28 for disposing of a plurality used needle retaining means 16. As illustrated in FIG. 14, the device 28 also enables the needle 16 and the end of the suture 27 to be hygienically and safely disposed. It is important to appreciate that the operator need not touch the needle 19 or suture 27, to remove the needle retaining means 16 from the forceps 11. The device 28 includes a housing 29 and a lid 30. The device also includes retaining means receiving portions 31. After suturing, the retaining means 16 could be detached and disposed of. For example, the lid 30 of the device 28 described above can be opened. The arm of the forceps 11 having the retaining means 16 attached, is pushed into a receptacle, which then grips the retaining means 16 with sufficient force so that when the arm of the forceps 11 is removed from the receiving portion 31, the retaining means 16 is retained in the disposal device 28. The disposal device 28 can then be closed with the assembly contained within it. If the surgeon wishes to re-use the retaining means 16 (and attached needle), the device is opened and the arm of the forceps 11 can be passed through the sleeve until the sleeve engages the ledge on the arm and is retained. The forceps 11 and the retaining means 16 (and needle) can then be withdrawn from the recess by manipulating/withdrawing the forceps 11. When desired, the disposal device 28 (holding one or more assemblies) can be closed and disposed of as a dirty unit. The forceps 11 can be sterilised and re-used in surgery.

As previously mentioned, the needle retaining means 16 may be permanently attached to the forceps 11. Any known method of permanent attachment may be adopted, provided the needle retaining means 16 is securely fastened/attached to the forceps.

It is to be appreciated that the forceps could be packaged in a sterile container and sold as a disposable unit.

It is apparent from the foregoing that various modifications can be made to the embodiments of this invention, without departing from the spirit and scope thereof. These modifications and the embodiments resulting therefrom, will be apparent to those skilled in the art, after reading this disclosure.

I claim:

1. A surgical forceps for gripping and manipulating a surgical needle comprising:
    a pair of arms, wherein each arm comprises a proximal hand gripping portion and a distal tissue manipulating portion;
    a needle retaining means for accepting and retaining a needle comprising
        a needle impervious, sleeve-shaped casing, which is connected to one of said arms, and
    from which one of the arms extends;
        wherein the needle retaining means is fully proximal to the distal end of said arm;
        and wherein the casing surrounds a separate needle pervious means for retaining a needle tip.

2. The surgical forceps of claim 1, wherein said needle retaining means is configured to orient a needle within an operative field.

3. The surgical forceps of claim 1, wherein the separate needle pervious means is formed of rubber or rubber-like material.

4. The surgical forceps of claim 1, wherein said separate needle pervious means is formed of silicone or silicone-like material.

5. The surgical forceps of claim 1, wherein said needle impervious casing is formed of metal or plastic.

* * * * *